United States Patent [19]

Sakata et al.

[11] Patent Number: 4,849,207
[45] Date of Patent: Jul. 18, 1989

[54] PORPHYRIN DERIVATIVES

[75] Inventors: Isao Sakata, Okayama; Susumu Nakajima, Hokkaido; Koichi Koshimizu, Nara; Natsuki Samejima, Hokkaido; Kazumi Inohara, Hiroshima; Hiroyuki Takata, Okayama; Hirohiko Yamauchi, Chiba; Nobuo Ueda, Chiba; Masaaki Hazue, Hyogo, all of Japan

[73] Assignees: Nihon Medi-Physics Co., Ltd., Hyogo; Toyo Hakka Kogyo Co., Ltd., Okayama, both of Japan

[21] Appl. No.: 922,492

[22] Filed: Oct. 23, 1986

[30] Foreign Application Priority Data

Oct. 23, 1985 [JP] Japan ................................ 60-235322
Oct. 23, 1985 [JP] Japan ................................ 60-235323

[51] Int. Cl.$^4$ .................. A61K 31/40; A61K 31/555; C07D 487/22
[52] U.S. Cl. .................................. 424/1.1; 514/185; 514/410; 534/10; 534/16; 540/145
[58] Field of Search .................. 540/145; 534/10, 16; 424/1.1, 9; 514/410, 185

[56] References Cited

U.S. PATENT DOCUMENTS

| | | | |
|---|---|---|---|
| 4,604,241 | 8/1986 | Sakata et al. | 540/145 |
| 4,634,557 | 1/1987 | Sato | 540/145 |
| 4,649,151 | 3/1987 | Dougherty et al. | 514/410 |
| 4,675,338 | 6/1987 | Bommer et al. | 514/410 |

*Primary Examiner*—Richard L. Raymond

[57] ABSTRACT

A porphyrin compound of the formula:

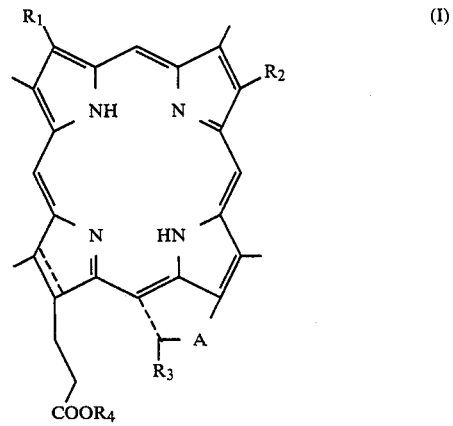

wherein $R_1$ and $R_2$ are each $-CH=CH_2$, $-CH_2CH_3$, $-CH(O\text{-lower alkanoyl})CH_3$, $-CH(OR)CH_3$ or $-CH(O\text{-lower alkylene-}OR)CH_3$; $R_3$ is $-H$, $-COOH$, $-COO\text{-lower alkyl}$, $-COO\text{-lower alkylene-}OR$ or $-COO\text{-lower alkylene-}OOC\text{-}Z$; $R_4$ is $-H$, -lower alkyl or -lower alkylene-OR; R is $-H$, -lower alkyl or a residue of a polyfunctional carboxyl compound excluding a hydrogen atom therefrom; Z is a residue of the compound of the formula (I) excluding $R_3$ therefrom; A is $-CH_2-$ or $-CO-$; and the dotted line from the gamma-position indicates no bonding or a single direct bond; and the dotted line between the 7- and 8-positions indicates the presence of a single bond or a double bond; and its complexes with a metal(s) in the porphine skeleton and/or at the residue of the polyfuntional carboxyl compound, at least one of $R_1$, $R_2$, $R_3$ and $R_4$ being a group containing R which represents the residue of the polyfunctional carboxyl compound and $R_1$ being capable of representing 1-iodoethyl in addition to said meanings when $R_3$ is $-COO\text{-lower alkylene-}OOC\text{-}Z$, which shows a high accumulation in the locus of cancer with quick excretion from normal tissues.

17 Claims, No Drawings

PORPHYRIN DERIVATIVES

The present invention relates to porphyrin derivatives, and their production and use. More particularly, it relates to novel porphyrin derivatives, and their preparation processes and their uses for diagnosis and therapy of cancer (or tumor).

In this specification, the term "porphyrin derivatives" are used in a broad sense and cover any compound having the following fundamental skeleton, which will be hereinafter referred to as "porphine skeleton":

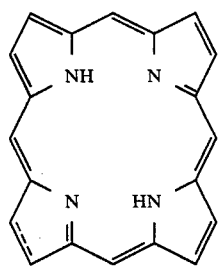

(A)

In the above skeleton, two hydrogen atoms or two protons attached to the nitrogen atoms in the pyrrole rings can be replaced by a metal atom or a metal ion to give the so-called "metalloporphyrin derivatives".

Porphyrin derivatives are known to have an affinity to cancerous tissues and exert a destructive effect thereon by application of an outer energy thereto. This characteristic property of porphyrin derivatives suggests their applicability towards the diagnosis and therapy of cancers. Unfortunately, however, considerable phototoxicity, i.e. toxicity caused by irradiation with light, is observed on porphyrin derivatives. Further, porphyrin derivatives are often hardly metabolized in or released from normal tissues. Of these defects, the former can be overcome to a certain extent by replacement of the protons attached to the nitrogen atoms in the pyrrole rings by some certain metal atoms (Japanese Patent Publication (unexamined) No. 83185/86). However, any proposal for overcoming the latter has not been made.

As a result of the extensive study, it has now been found that the introduction of the residue of a polyfunctional carboxyl compound into the molecule of a porphyrin compound makes it possible to release the resulting porphyrin derivative quickly from normal tissues while retaining a high accumulability in the locus of cancer. This quick release from normal tissues can contribute in inhibition of said photo-toxicity. This invention is based on the above finding.

According to the present invention, there are provided porphyrin compounds of the formula:

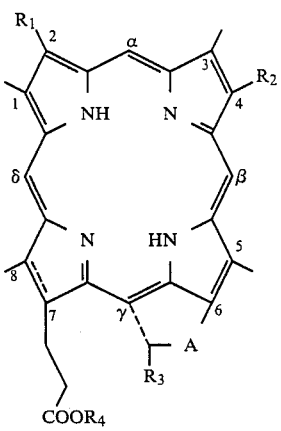

(I)

wherein
$R_1$ and $R_2$ are each —CH=CH$_2$, —CH$_2$CH$_3$, —CH-(O-lower alkanoyl)CH$_3$, —CH(OR)CH$_3$ or —CH-(O-lower alkylene-OR)CH$_3$;

$R_3$ is —H, —COOH, —COO-lower alkyl, —COO-lower alkylene-OR or —COO-lower alkylene-OOC-Z;

$R_4$ is —H, -lower alkyl or -lower alkylene-OR;

R is —H, -lower alkyl or a residue of a polyfunctional carboxyl compound excluding a hydrogen atom therefrom;

Z is a residue of the compound of the formula (I) excluding $R_3$ therefrom;

A is —CH$_2$— or —CO—;

the dotted line from the gamma-position indicates no bonding or a single direct bond; and the dotted line between the 7- and 8-positions indicates the presence of a single bond or a double bond;

and their complexes with metals in the porphine skeleton and/or at the residue of the polyfunctional carboxyl compound, at least one of $R_1$, $R_2$, $R_3$ and $R_4$ being a group containing R which represents the residue of the polyfunctional carboxyl compound and $R_1$ being capable of representing 1-iodoethyl in addition to said meanings when $R_3$ is —COO-lower alkylene-OOC-Z In the above definitions of the symbols, the term "lower alkylene" means alkylene having usually not more than 5 carbon atoms, preferably from 1 to 3 carbon atoms (e.g. ethylene, trimethylene, propylene). The term "lower alkyl" is intended to mean alkyl having usually not more than 8 carbon atoms, preferably from 1 to 3 carbon atoms (e.g. methyl, ethyl, n-propyl, isopropyl). The term "lower alkanoyl" is intended to mean alkanoyl having normally not more than 8 carbon atoms, preferably from not more than 3 carbon atoms (e.g. acetyl, propionyl).

The term "polyfunctional carboxyl compound" means any carboxylic acid having at least one functional group (e.g. —NH$_2$, —OH, —SH, —COOH) in addition to the carboxyl group. Preferably, it is a physiologically acceptable one such as an amino acid (e.g. glycine, cysteine, glutamic acid, alanine, cystine, asparagine, valine, methionine, glutamine, leucine, phenylalanine, isoleucine, serine, tryptophane, threonine, aspartic acid). More preferably, it is a physiologically acceptable one having at least one chelate-forming group in addition to the carboxyl group, of which examples are ethylenediamine tetraacetic acid (EDTA), diethylenetriaminepentaacetic acid (DTPA), 1,2-bis(o-aminophenoxy)ethane-N,N,N',N'-tetraacetic acid (BAPTA), 1,3-diaminopropan-2-ol-N,N,N',N'-tetraacetic acid (DPTA-OH), trans-1,2-cyclohexanediamine-N,N,N',N'-tetraacetic acid (CyDTA), N-hydroxyethylethylenediamine-N,N',N'-triacetic acid (EDTA-OH), ethylenediamine-N,N'-diacetic acid (EDDA), iminodiacetic acid (IDA), ethylenediamine-di(o-hydroxyphenylacetic acid) (EDDHA), etc. These may be used in the form of alkali metal salts.

The porphyrin compounds of the formula (I) cover at least two groups, i.e. those of the formula (I) wherein A is —$CH_2$—, the dotted line from the gamma-position indicates no bonding and the dotted line between the 7- and 8-positions indicates the presence of a double bond (porphines), and those of the formula (I) wherein A is —CO—, the dotted line from the gamma position indicates a single direct bond and the dotted line between the 7- and 8-positions indicates the presence of a single bond (phorbines).

When the polyfunctional carboxyl compound has a chelate-forming group, the metal complexes of the porphyrin compounds (I) cover at least three groups, i.e. those having a metal only in the porphine skeleton, those having a metal at the residue of the polyfunctional carboxyl compound and those having metal atoms in the porphine skeleton and at the residue of the polyfunctional carboxyl compound.

The porphyrin compounds (I) as above defined and their metal complexes are novel and can be produced by per se conventional procedures. Usually, they may be produced by (a) constructing the porphyrin compounds which correspond to the formula (I) but at least one of $R_1$, $R_2$, $R_3$ and $R_4$ represents a group containing R=H and (b) introducing the residue of the polyfunctional carboxyl compound as R into the constructed porphyrin compounds, optionally (c) complexing and/or chelating with a metal(s) before and/or after said introduction.

The constructing step may be effected by application of per se conventional procedures as disclosed in Osa et al: "Porphyrin No Kagaku (Chemistry of Porphyrins)" published by Kyoritsu Shuppan in 1982; Falk: "Porphyrins and Metalloporphyrins" published by Elsevier in 1975; Dolphin: "The Porphyrins", published by Academic Press in 1978, etc. For instance, the construction of the porphyrin compounds corresponding to the formula (I) but at least one of $R_1$, $R_2$, $R_3$ and $R_4$ represents a group containing R=H may be accomplished in the manner as disclosed in Japanese Patent Publications (unexamined) Nos. 7279/86 and 83185/86. Instead of artificial construction, the same substances as the constructed porphyrin compounds may be obtained from natural sources including plants (phorbines) and animals (porphines).

The constructed porphyrin compounds are then reacted with the polyfunctional carboxyl compound or its reactive derivative at any of their side chain to give the porphyrin compounds (I). This reaction is usually carried out in an inert solvent. When desired, such a reaction-promoting or condensing agent as a dehydrating agent or an acid-eliminating agent may be employed.

In the case that the polyfunctional carboxyl compound is a carboxylic acid having a chelate-forming group, it is usually introduced into the hydroxyl group present in the porphyrin compounds. The reaction is thus the condensation between the carboxyl group in the carboxylic acid and the hydroxyl group in the porphyrin compounds. Those functional groups may be previously converted into any other reactive groups. In the case that the polyfunctional carboxyl compound is an amino acid, it is usually introduced into the carboxyl group present in the porphyrin compounds. The reaction is thus the condensation between the amino group in the amino acid and the carboxyl group in the porphyrin compounds. These functional groups may be converted into any other reactive groups prior to the reaction.

Before or after the above reaction for introduction of the residue of the polyfunctional carboxyl compound as R, the complexing with a metal in the porphine skeleton and/or chelating with a metal at the residue of the polyfunctional carboxyl compound may be accomplished by treatment with an appropriate salt(s) of such metal(s). Examples of the metals are Si, Mn, Fe, Co, Ni, Zn, Ga, In, Sn, Sm, Eu, Gd, Tc, Ti, etc. Depending upon the kind of the metal, the behavior on the complexing or chelating is different. Further, at least one of the metals is preferred to be radioactive for the use in diagnosis or therapy of cancer. Preferred examples of the radioactive metal are $^{67}$Ga, $^{111}$In, $^{201}$Tl, $^{99m}$Tc. Favorable examples of the non-radioactive metal are Si, Co, Ni, Zn, Ga, In, Sn, etc.

Production of the porphyrin compounds (I) and their metal complexes will be hereinafter explained more in details by way of some typical examples.

When the polyfunctional carboxyl compound is DTPA (diethylenetriaminepentaacetic acid), the porphyrin compounds not having the DTPA residue as R or their metal complexes having the metal in the porphine skeleton disclosed in Japanese Patent Publications (unexamined) Nos. 7279/86 and 83185/86 are reacted with DTPA, for instance, in pyridine under heating. Examples of the porphyrin compounds (I) and their metal complexes thus produced are as follows:

(1) Ethylene glycol monodiethylenetriaminetetraacetic acid-acetate mono-10b-methylpheophorbate (hereinafter referred to as "DTPA-10EG PPB-Me");

(2) 2-Desethenyl-2-[1-(diethylenetriamiene-tetraacetic acid-acetyloxyethane)oxyethyl] methylpheophorbide (hereinafter referred to as "DTPA-2EG PPB-Me");

(3) Ethylene glycol mono-diethylenetriaminetetraacetic acid-acetate mono-7c-pyropheophorbate (hereinafter referred to as "DTPA-7EG pyroPPB");

(4) Ethylene glycol mono-diethylenetriaminetetraacetic acid-acetate mono-7c-pheophorbate (hereinafter referred to as "DTPA-7EG PPB");

(5) Ethylene glycol mono-diethylenetriamine-tetraacetic acid-acetate mono-10b-pheophorbate (hereinafter referred to as "DTPA-10EG PPB");

(6) 2-[1-Diethylenetriamine-tetraacetic acidacetyloxyethane)oxyethyl]-4-[1-(2-hydroxyethyl)oxyethyl]-methyl deuteroporphyrin (hereinafter referred to as "DTPA-EG DP-Me");

(7) 2-[1-(Diethylenetriamine-tetraacetic acid-acetyloxyethane)oxyethyl]-4-[1-(2-hydroxyethyl)oxyethyl] deuteroporphyrin (hereinafter referred to as "monoDTPA-EG DP");

(8) 2,4-Bis[1-(diethylenetriamine-tetraacetic acid-acetyloxyethane)oxyethyl] deuteroporphyrin (hereinafter referred to as "bisDTPA-EG DP");

(9) 2-[1-(Diethylenetriamine-tetraacetic acid-acetyloxyethane)oxyethyl]-4-[1-(2-hydroxyethyl)oxyethyl] Ga-deuteroporphyrin (hereinafter referred to as "monoDTPA-EG Ga-DP");

(10) 2,4-Bis[1-(diethylenetriamine-tetraacetic acid-acetyloxyethane)oxyethyl] Ga-deuteroporphyrin (hereinafter referred to as "bisDTPA-EG Ga-DP");

(11) 2-[1-(Diethylenetriamine-tetraacetic acidacetyloxyethane)oxyethyl]-4-[1-(2-hydroxyethyl)oxyethyl] In-deuteroporphyrin (hereinafter referred to as "monoDTPA-EG In-DP");

(12) 2,4-Bis[1-(diethylenetriamine-tetraacetic acid-acetyloxyethane)oxyethyl] In-deuteroporphyrin (hereinafter referred to as "bisDTPA-EG In-DP"), etc.

The above obtained porphyrin compounds (I) and their metal complexes in the porphine skeleton are treated with a metal compound such as a metal halide (e.g. $InCl_3$, $SmCl_3$, $EuCl_3$, $GdCl_3$) in a mixture of chloroform and methanol, whereby the metal is captured by the chelate-forming group, in the DTPA residue to give the complexes of the porphyrin compounds (I) having the metal at the DTPA residue. Examples of the thus produced metal complexes of the porphyrin compounds (I) are as follows:

(13) Ethylene glycol In-monodiethylenetriaminetetraacetic acid-acetate mono-10b-methylpheophorbate (hereinafter referred to as "In-DTPA-10EG PPB-Me");

(14) Ethylene glycol In-mono-diethylenetriaminetetraacetic acid-acetate mono-7c-pyropheophorbate (hereinafter referred to as "In-DTPA-7EG pyroPPB");

(15) 2-[1-(In-Diethylenetriamine-tetraacetic acid-acetyloxyethane)oxyethyl]-4-[1-(2-hydroxyethyl)oxyethyl] deuteroporphyrin dimethyl ester (hereinafter referred to as "In-DTPA-EG DP-Me");

(16) 2-[1-(In-Diethylenetriamine-tetraacetic acid-acetyloxyethane)oxyethyl]-4-[1-(2-hydroxyethyl)oxyethyl] deuteroporphyrin (hereinafter referred to as "In-monoDTPA-EG DP");

(17) 2,4-Bis[1-(In-diethylenetriamine-tetraacetic acid-acetyloxyethane)oxyethyl] deuteroporphyrin (hereinafter referred to as "In-bisDTPA-EG DP");

(18) 2-[1-(Sm-Diethylenetriamine-tetraacetic acid-acetyloxyethane)oxyethyl]-4-[1-(2-hydroxyethyl)oxyethyl] deuteroporphyrin (hereinafter referred to as "Sm-DTPA-EG DP");

(19) 2-[1-(Eu-Diethylenetriamine-tetraacetic acid-acetyloxyethane)oxyethyl]-4-[1-(2-hydroxyethyl)oxyethyl] deuteroporphyrin (hereinafter referred to as "Eu-DTPA-EG DP");

(20) 2-[1-(Gd-Diethylenetriamine-tetraacetic acid-acetyloxyethane)oxyethyl]-4-[1-(2-hydroxyethyl)oxyethyl] deuteroporphyrin dimethyl ester (hereinafter referred to as "Gd-DTPA-EG DP-Me");

(21) 2-[1-(Gd-Diethylenetriamine-tetraacetic acid-acetyloxyethane)oxyethyl]-4-[1-(2-hydroxyethyl)oxyethyl] deuteroporphyrin (hereinafter referred to as "Gd-DTPA-EG DP");

(22) 2-[1-(In-Diethylenetriamine-tetraacetic acid-acetyloxyethane)oxyethyl]-4-[1-(2-hydroxyethyl)oxyethyl] Ga-deuteroporphyrin (hereinafter referred to as "In-monoDTPA-EG Ga-DP");

(23) 2,4-Bis[1-(In-diethylenetriamine-tetraacetic acid-acetyloxyethane)oxyethyl] Ga-deuteroporphyrin (hereinafter referred to as "In-bisDTPA-EG Ga-DP");

(24) 2-[1-(In-Diethylenetriamine-tetraacetic acid-acetyloxyethane)oxyethyl]-4-[1-(2-hydroxyethyl)oxyethyl] In-deuteroporphyrin (hereinafter referred to as "In-monoDTPA-EG In-DP");

(25) 2,4-Bis[1-(In-diethylenetriamine-tetraacetic acid-acetyloxyethane)oxyethyl] In-deuteroporphyrin (hereinafter referred to as "In-bisDTPA-EG In-DP");

(26) 2-[1-(Gd-Diethylenetriamine-tetraacetic acid-acetyloxyethane)oxyethyl]-4-[1-(2-hydroxyethyl)oxyethyl] Ga-deuteroporphyrin (hereinafter referred to as "Gd-monoDTPA-EG Ga-DP");

(27) 2,4-Bis[1-(Gd-diethylenetriamine-tetraacetic acid-acetyloxyethane)oxyethyl] Ga-deuteroporphyrin (hereinafter referred to as "Gd-bisDTPA-EG Ga-DP");

(28) 2-[1-(Ga-Diethylenetriamine-tetraacetic acid-acetyloxyethane)oxyethyl]-4-[1-(2-hydroxyethyl)oxyethyl] Ga-deuteroporphyrin (hereinafter referred to as "Ga-monoDTPA-EG Ga-DP");

(29) 2,4-Bis[1-(Ga-diethylenetriamine-tetraacetic acid-acetyloxyethane)oxyethyl] Ga-deuteroporphyrin (hereinafter referred to as "Ga-bisDTPA-EG Ga-DP"), etc.

When the polyfunctional carboxyl compound is glycine or glutamic acid, the porphyrin compounds not having the glycine or glutamic acid residue as R disclosed in Japanese Patent Publications (unexamined) Nos. 7279/86 and 83185/86 are reacted with glycine or glutamic acid in an inert solvent (e.g. chloroform) in the presence of a condensing agent (e.g. dicyclohexylcarbodiimide (DCC)). In this case, the starting porphyrin compounds are preferred to be subjected to reaction in the form of dicyclohexylamine (DCHA) salt, while the reagent glycine or glutamic acid is favored to be used in the form of lower alkyl ester (e.g. ethyl ester). Examples of the porphyrin compounds (I) thus produced are as follows:

(30) Hematoporphinyl diglycine (hereinafter referred to as "HP-Gly");

(31) Hematoporphinyl diglutamic acid (hereinafter referred to as "HP-Glu");

(32) Diacetylhematoporphinyl diglycine (hereinafter referred to as "HDA-Gly");

(33) Diacetylhematoporphinyl diglutamic acid (hereinafter referred to as "HDA-Glu"), etc.

The above obtained porphyrin compounds (I) are treated with a metal compound such as a metal halide (e.g. $InCl_3$) in acetic acid while heating to give the complexes of the porphyrin compounds (I) having the metal in the porphine skeleton. Examples of the thus produced metal complexes of the porphyrin compounds (I) are as follows:

(34) In-Hematoporphinyl diglycine (hereinafter referred to as "In-HP-Gly");

(35) In-Hematoporphinyl diglutamic acid (hereinafter referred to as "In-HP-Glu");

(36) In-Diacetylhematoporphinyl diglycine (hereinafter referred to as "In-HDA-Gly");

(37) In-Diacetylhematoporphinyl diglutamic acid (hereinafter referred to as "In-HDA-Glu"), etc.

The metal complexes of the porphyrin compounds (I) wherein the metal is radioactive may be prepared from the corresponding porphyrin compounds (I) in the same manner as above. When the radioactive metal is $^{67}Ga$, $^{111}In$ or $^{201}Tl$, their chlorides such as $^{67}GaCl_3$, $^{111}InCl$ and $^{201}TlCl_3$ may be used as the reagents. When the radioactive metal is $^{99m}Tc$, its pertechnetate (e.g. $Na^{99m}TcO_4$) may be used in combination with a reducing agent (e.g. sodium hydrosulfite, stannous chloride). Examples of the thus produced metal complexes of the porphyrin compounds (I) are as follows:

(38) $^{111}In$-Hematoporphinyl diglycine (hereinafter referred to as "$^{111}In$-HP-Gly");

(39) $^{111}In$-Hematoporphinyl diglutamic acid (hereinafter referred to as "$^{111}In$-HP-Glu");

(40) $^{111}$In-Diacetylhematoporphinyl diglutamic acid (hereinafter referred to as "$^{111}$In-HDA-Glu");

(41) $^{67}$Ga-Hematoporphinyl diglycine (hereinafter referred to as "$^{67}$Ga-HP-Gly");

(42) $^{67}$Ga-Hematoporphinyl diglutamic acid (hereinafter referred to as "$^{67}$Ga-HP-Glu");

(43) $^{67}$Ga-Diacetylhematoporphinyl diglutamic acid (hereinafter referred to as "$^{67}$Ga-HDA-Glu");

(44) $^{201}$Tl-Hematoporphinyl diglycine (hereinafter referred to as "$^{201}$Tl-HP-Gly");

(45) $^{201}$Tl-Hematoporphinyl diglutamic acid (hereinafter referred to as "$^{201}$In-HP-Glu");

(46) $^{201}$Tl-Diacetylhematoporphinyl diglutamic acid (hereinafter referred to as "$^{201}$Tl-HDA-Glu");

(47) Ethylene glycol $^{111}$In-monodiethylenetriamine-tetraacetic acid-acetate mono-10b-methylpheophorbate (hereinafter referred to as "$^{111}$In-DTPA-10EG PPB-Me");

(48) 2-[1-($^{111}$In-Diethylenetriamine-tetraacetic acid-acetyloxyethane)oxyethyl]-4-[1-(2-hydroxyethyl)oxyethyl] deuteroporphyrin dimethyl ester (hereinafter referred to as "$^{111}$In-DTPA-EG DP-Me");

(49) 2-[1-($^{111}$In-Diethylenetriamine-tetraacetic acid-acetyloxyethane)oxyethyl]-4-[1-(2-hydroxyethyl)oxyethyl] deuteroporphyrin (hereinafter referred to as "$^{111}$In-monoDTPA-EG DP");

(50) 2,4-Bis[1-($^{111}$In-diethylenetriamine-tetraacetic acid-acetyloxyethane)oxyethyl] deuteroporphyrin (hereinafter referred to as "$^{111}$In-bisDTPA-EG DP");

(51) 2-[1-($^{111}$In-diethylenetriamine-tetraacetic acid-acetyloxyethane)oxyethyl]-4-[1-(2-hydroxyethyl)oxyethyl] Ga-deuteroporphyrin (hereinafter referred to as "$^{111}$In-monoDTPA-EG Ga-DP");

(52) 2,4-Bis[1-($^{111}$In-diethylenetriamine-tetraacetic acid-acetyloxyethane)oxyethyl] Ga-deuteroporphyrin (hereinafter referred to as "$^{111}$In-bisDTPA-EG Ga-DP");

(53) Ethylene glycol $^{67}$Ga-monodiethylenetriamine-tetraacetic acid-acetate mono-10b-methylpheophorbate (hereinafter referred to as "$^{67}$Ga-DTPA-10EG PPB-Me");

(54) 2-[1-($^{67}$Ga-Diethylenetriamine-tetraacetic acid-acetyloxyethane)oxyethyl]-4-[1-(2-hydroxyethyl)oxyethyl] deuteroporphyrin dimethyl ester (hereinafter referred to as "$^{67}$Ga-DTPA-EG DP-Me");

(55) 2-[1-($^{67}$Ga-Diethylenetriamine-tetraacetic acid-acetyloxyethane)oxyethyl]-4-[1-(2-hydroxyethyl)oxyethyl] deuteroporphyrin (hereinafter referred to as "$^{67}$Ga-monoDTPA-EG DP");

(56) 2,4-Bis[1-($^{67}$Ga-diethylenetriamine-tetraacetic acid-acetyloxyethane)oxyethyl] deuteroporphyrin (hereinafter referred to as "$^{67}$Ga-bisDTPA-EG DP");

(57) 2-[1-($^{67}$Ga-Diethylenetriamine-tetraacetic acid-acetyloxyethane)oxyethyl]-4-[1-(2-hydroxyethyl)oxyethyl] Ga-deuteroporphyrin (hereinafter referred to as "$^{67}$Ga-monoDTPA-EG Ga-DP");

(58) 2,4-Bis[1-($^{67}$Ga-diethylenetriamine-tetraacetic acid-acetyloxyethane)oxyethyl] Ga-deuteroporphyrin (hereinafter referred to as "$^{67}$Ga-bisDTPA-EG Ga-DP");

(59) Ethylene glycol $^{201}$Tl-monodiethylenetriamine-tetraacetic acid-acetate mono-10b-methylpheophorbate (hereinafter referred to as "$^{201}$Tl-DTPA-10EG PPB-Me");

(60) 2-[1-($^{201}$Tl-Diethylenetriamine-tetraacetic acid-acetyloxyethane)oxyethyl]-4-[1-(2-hydroxyethyl)oxyethyl] deuteroporphyrin dimethyl ester (hereinafter referred to as "$^{201}$Tl-DTPA-EG DP-Me");

(61) 2-[1-($^{20}$Tl-diethylenetriamine-tetraacetic acid-acetyloxyethane)oxyethyl]-4-[1-(2-hydroxyethyl)oxyethyl] deuteroporphyrin (hereinafter referred to as "$^{201}$Tl-monoDTPA-EG DP");

(62) 2,4-Bis[1-($^{201}$Tl-diethylenetriamine-tetraacetic acid-acetyloxyethane)oxyethyl] deuteroporphyrin (hereinafter referred to as "$^{201}$Tl-bisDTPA-EG DP");

(63) 2-[1-($^{201}$Tl-Diethylenetriamine-tetraacetic acid-acetyloxyethane)oxyethyl]-4-[1-(2-hydroxyethyl)oxyethyl] Ga-deuteroporphyrin (hereinafter referred to as "$^{201}$Tl-monoDTPA-EG Ga-DP");

(64) 2,4-Bis[1-($^{201}$Tl-diethylenetriamine-tetraacetic acid-acetyloxyethane)oxyethyl] Ga-deuteroporphyrin (hereinafter referred to as "$^{201}$Tl-bisDTPA-EG Ga-DP");

(65) Ethylene glycol $^{99m}$Tc-monodiethylenetriamine-tetraacetic acid-acetate mono-10b-methylpheophorbate (hereinafter referred to as "$^{99m}$Tc-DTPA-10EG PPB-Me");

(66) 2-[1-($^{99m}$Tc-Diethylenetriamine-tetraacetic acid-acetyloxyethane)oxyethyl]-4-[1-(2-hydroxyethyl)oxyethyl] deuteroporphyrin dimethyl ester (hereinafter referred to as "$^{99m}$Tc-DTPA-EG DP-Me");

(67) 2-[1-($^{99m}$Tc-Diethylenetriamine-tetraacetic acid-acetyloxyethane)oxyethyl]-4-[1-(2-hydroxyethyl)oxyethyl] deuteroporphyrin (hereinafter referred to as "$^{99m}$Tc-monoDTPA-EG DP");

(68) 2,4-Bis[1-($^{99m}$Tc-diethylenetriamine-tetraacetic acid-acetyloxyethane)oxyethyl] deuteroporphyrin (hereinafter referred to as "$^{99m}$Tc-bisDTPA-EG DP");

(69) 2-[1-($^{99m}$Tc-Diethylenetriamine-tetraacetic acid-acetyloxyethane)oxyethyl]-4-[1-(2-hydroxyethyl)oxyethyl Ga-deuteroporphyrin (hereinafter referred to as "$^{99m}$Tc-monoDTPA-EG Ga-DP");

(70) 2,4-Bis[1-$^{99m}$Tc-diethylenetriamine-tetracetic acid-acetyloxyethane)oxyethyl] Ga-deuteroporphyrin (hereinafter referred to as "$^{99m}$Tc-bisDTPA-EG Ga-DP"), etc.

The iodinated porphyrin compounds of the formula (I) wherein $R_1$ represents 1-iodoethyl and $R_3$ is —COO-lower alkylene-OOC-Z and their metal complexes may be produced, for instance, by reacting the corresponding 2-ethenyl porphyrin compounds or their metal complexes with hydrogen bromide and reacting the resulting 2-(1-bromoethyl) product with sodium iodide in an inert solvent (e.g. acetone), optionally followed by complexing and/or chelating with a metal(s). A typical example of the thus produced iodinated porphyrin compounds is as follows:

(71) Bis[2-desethenyl-2-(1-iodoethyl)pheophobide]ethylene glycol diester (hereinafter referred to as "I$_2$ PPB dimer").

The porphyrin compounds (I) and their metal complexes of this invention can be accumulated at the locus of cancer with high selectivity and released therefrom with a slow rate. They hardly react when light is applied but are reacted easily on irradiation with microwave or electro-microwave to produce single state oxygen, by which cancer cells are destructed. Since they are quickly released and excreted from normal tissues, any harmful effect is not exerted on normal cells.

As stated above, the porphyrin compounds (I) and their metal complexes of the invention are retained in cancerous tissues over a long period of time but quickly released and excreted from normal tissues. Therefore, it is substantially unnecessary to take care on photo-toxicity as produced by conventional porphyrin compounds.

Accordingly, the porphyrin compounds (I) and their metal complexes of the invention are useful as diagnostic agents, tumor markers, carriers for anti-tumor agents, etc.

Practical and presently preferred embodiments of the invention are illustratively shown in the following Examples wherein part(s) and % are by weight.

EXAMPLE 1

Laser irradiation to an extracted organ (excited fluorescent spectrum):

To each of golden hamsters (five animals being grouped) transplaned with nitrosoamine-induced cancer cells of the pancreas, DTPA-10EG PPB-Me (5 mg) diluted with 0.1M citrate buffer (1 ml) was administered intravenously 14 to 21 days after the transplantation, and cancer cells and other organs were extracted. To each of the organs as extracted, $N_2$-pulsed laser ($N_2$ 337 nm, 2 ns 400–1000 nm) was irradiated, and excited fluorescent spectrum was measured after 24 hours. Taking the peak wavelength of NADH at 470 nm as the standard (i.e. 1), the wavelength at 600 to 900 nm was calculated. The results are shown in Table 1, from which it is understood that a porphyrin-related substance has a remarkably selective affinity to cancer cells.

HOAc (5:2)) at Rf=about 0.6. After completion of the reaction, excessive DTPA was removed by filtration. To the filtrate, ethyl acetate was added, and the precipitated crystals were collected by filtration and subjected to column chromatography on silicic acid (ethyl acetate-methanol) to give DTPA-10EG PPB-Me (0.5 g). Yield, 31.4%.

EXAMPLE 3

2-Desethenyl-2-[1-(2-hydroxyethyl)oxyethyl] methylpheophorbide (1 g) was dissolved in collidine (50 ml), DTPA (1 g) was added thereto, and the resultant mixture was heated at 50° C. under reduced pressure for 2 hours, followed by treatment as in Example 2 to give DTPA-2EG PPB-Me (0.2 g). Yield, 12.5%.

EXAMPLE 4

Ethylene glycol mono-7c-pyropheophorbide (1 g) was dissolved in picoline (60 ml), DTPA (1 g) was added thereto, and the resultant mixture was allowed to stand at room temperature for 1 week, followed by treatment as in Example 2 to give DTPA-7EG pyroPPB (0.1 g). Yield, 6.1%.

EXAMPLE 5

Ethylene glycol mono-7c-pheophorbide (1 g) was dissolved in dimethylformamide (50 ml), DTPA (1.5 g)

TABLE 1

| No. | Compound | | Cancer | Liver | Lung | Kidney | Serum |
|---|---|---|---|---|---|---|---|
| 1 | DTPA—10EG PPB—Me | | 2.73 | 0.69 | 0.47 | 0.37 | 0.53 |
| 2 | DTPA—2EG PPB—Me | | 1.32 | 0.93 | 1.00 | 0.31 | 0.42 |
| 3 | DTPA—7EG pyroPPB | | 2.20 | 0.87 | 1.23 | 0.25 | 0.39 |
| 4 | DTPA—7EG PPB | | 0.53 | 0.33 | 0.30 | 0.32 | 0.31 |
| 5 | DTPA—10EG PPB | | 1.20 | 0.77 | 0.45 | 0.43 | 0.52 |
| 6 | DTPA—EG DP—Me | | 0.76 | 0.09 | 0.08 | 0.08 | 0.32 |
| 7 | mono-DTPA—EG DP | mixture | 1.00 | 0.08 | 0.14 | 0.25 | 0.89 |
| 8 | bisDTPA—EG DP | | | | | | |
| 9 | monoDTPA—EG Ga—DP | | 0.83 | 0.19 | 0.06 | 0.33 | 1.21 |
| 10 | bisDTPA—EG Ga—DP | | 0.86 | 0.15 | 0.06 | 0.10 | 0.34 |
| 11 | monoDTPA—EG In—DP | | 0.39 | 0.03 | 0.15 | 0.00 | 0.16 |
| 12 | bisDTPA—EG In—DP | | 0.47 | 0.12 | 0.13 | 0.13 | 0.18 |
| 13 | In—DTPA—10EG PPB—Me | | 1.03 | 0.43 | 0.19 | 0.12 | 0.34 |
| 14 | In—DTPA—7EG pyroPPB | | 1.25 | 0.52 | 0.47 | 0.42 | 0.45 |
| 15 | In—DTPA—EG DP—Me | | 0.83 | 0.36 | 0.09 | 0.15 | 0.71 |
| 16 | In—monoDTPA—EG DP | mixture | 1.00 | 0.20 | 0.13 | 0.14 | 0.67 |
| 17 | In—bisDTPA—EG DP | | | | | | |
| 18 | Sm—DTPA—EG DP | | 1.07 | 0.10 | 0.12 | 0.11 | 0.85 |
| 19 | Eu—DTPA—EG DP | | 1.33 | 0.09 | 0.14 | 0.03 | 0.43 |
| 20 | Gd—DTPA—EG DP—Me | | 0.60 | 0.12 | 0.07 | 0.05 | |
| 21 | Gd—DTPA—EG DP | | 2.10 | 0.26 | 0.14 | 0.03 | 1.00 |
| 22 | In—monoDTPA—EG Ga—DP | | 0.50 | 0.03 | 0.14 | 0.05 | 0.02 |
| 23 | In—bisDTPA—EG Ga—DP | | 0.40 | 0.18 | — | 0.10 | 0.03 |
| 24 | In—monoDTPA—EG In—DP | | 0.30 | 0.07 | 0.09 | 0.00 | 0.24 |
| 25 | In—bisDTPA—EG In—DP | | 0.00 | 0.25 | 0.05 | 0.05 | 0.05 |
| 30 | HP—Gly | | 1.94 | 0.39 | 0.35 | 0.32 | 3.51 |
| 31 | HP—Glu | | 1.79 | 0.45 | 0.37 | 0.33 | 5.43 |
| 32 | HDA—Gly | | 2.20 | 0.33 | 0.86 | 0.39 | 5.62 |
| 33 | HDA—Glu | | 2.69 | 0.33 | 1.09 | 0.36 | 5.12 |
| 34 | In—HP—Gly | | 0.29 | 0.01 | 0.03 | 0.08 | 0.32 |
| 35 | In—HP—Glu | | 0.40 | 0.21 | 0.10 | 0.06 | 0.90 |
| 36 | In—HDA—Gly | | 1.20 | 0.16 | 0.50 | 0.36 | 4.06 |
| 37 | In—HDA—Glu | | 2.90 | 0.35 | 0.33 | 0.20 | 7.39 |
| 71 | $I_2$ PPB Dimer | | 0.82 | 0.31 | 0.20 | 0.07 | 1.58 |

EXAMPLE 2

To a solution of ethylene glycol mono-10b-methyl pheophorbide (1 g) in pyridine (50 ml), DTPA (1.5 g) was added, and the resultant mixture was heated while stirring for 3 hours. The end point of the reaction was confirmed by detection of the product on TLC (MeOHand silica gel (1 g) were added thereto, and the resultant mixture was heated while stirring, followed by treatment as in Example 2 to give DTPA-7EG PPB (0.1 g). Yield, 6.3%.

EXAMPLE 6

Ethylene glycol mono-10b-pheophorbide (1 g) was dissolved in pyridine (50 ml), DTPA (1.5 g) and zeolite (1 g) were added thereto, and the resultant mixture was heated while stirring, followed by treatment as in Example 2 to give DTPA-10EG PPB (0.4 g). Yield, 25%.

EXAMPLE 7

2,4-Bis[1-(2-hydroxyethyl)oxyethyl]methyldeuteroporphyrin (1 g) was dissolved in picoline (50 ml), DTPA (1.0 g) was added thereto, and the resultant mixture was heated while stirring, followed by treatment as in Example 2 to give DTPA-EG DP-Me (0.6 g). Yield, 37.7%.

EXAMPLE 8

2,4-Bis[1-(2-hydroxyethyl)oxyethyl]methyldeuteroporphyrin (1 g) was dissolved in pyridine (70 ml), DTPA (1.0 g) was added thereto, and the resultant mixture was heated while stirring. The end point of the reaction was confirmed by detection of the products on TLC (MeOH-HOAc (5:2)) at Rf=about 0.6 and at Rf=about 0.3. Then, treatment was carried out in the same manner as in Example 2. On column chromatography on silicic acid (ethyl acetate-methanol), there were obtained said two products, i.e. mono-DTPA-EG DP (0.4 g; yield, 25.8%) and bisDTPA-EG DP (0.4 g; yield, 19.1%).

EXAMPLE 9

2,4-Bis[1-(2-hydroxyethyl)oxyethyl] Ga-deuteroporphyrin (1 g) was dissolved in pyridine (70 ml), DTPA (1.0 g) was added thereto, and the resultant mixture was heated under reduced pressure, followed by treatment as in Example 8 to give monoDTPA-EG Ga-DP (0.3 g; yield, 20.3%) and bisDTPA-EG Ga-DP (0.3 g; yield, 15.4%).

EXAMPLE 10

2,4-Bis[2-(1-hydroxyethyl)oxyethyl] In-deuteroporphyrin (1 g) was dissolved in collidine (70 ml), DTPA (1.0 g) was added thereto, and the resultant mixture was heated while stirring, followed by treatment as in Example 8 to give monoDTPA-EG In-DP (0.5 g; yield, 35.5%) and bisDTPA-EG In-DP (0.4 g; yield, 22.0%).

EXAMPLE 11

Each (1 g) of the following compounds obtained in EXAMPLEs 2, 4, 7, 8, 9 and 10 was dissolved in $CHCl_3$-MeOH (3:1) (100 ml): DTPA-10EG PPB-Me, DTPA-7EG pyroPPB, DTPA-EG DP-Me, monoDTPA-EG DP, bisDTPA-EG DP, monoDTPA-EG Ga-DP, bisDTPA-EG Ga-DP, monoDTPA-EG In-DP and bisDTPA-EG In-DP. A solution of a theoretical amount of $InCl_3$ in water (2 ml) was added thereto, whereby a complex was produced immediately (confirmed by TLC, macroscopic observation and UV handscope). The reaction mixture was concentrated under reduced pressure to driness to give each of the following compounds in a yield of 100%: In-DTPA-10EG PPB-Me, In-DTPA-7EG pyroPPB, In-DTPA-EG DP-Me, In-monoDTPA-EG DP, In-bisDTPA-EG DP, In-monoDTPA-EG Ga-DP, In-bisDTPA-EG Ga-DP, In-monoDTPA-EG In-DP and In-bisDTPA-EG In-DP.

EXAMPLE 12

DTPA-EG DP (a mixture of the mono compound and the bis compound in a weight ratio of 3:1) (1 g) as obtained in Example 8 was dissolved in $CHCl_3$-MeOH (4:1) (100 ml), and a theoretical amount of $SmCl_3$, $EuCl_3$ or $GdCl_3$ dissolved in water (2 ml) was added thereto to form a complex. The reaction mixture was treated as in Example 11 to give each of the following compounds in a yield of 100%: Sm-DTPA-EG DP, Eu-DTPA-EG DP and Gd-DTPA-EG DP.

EXAMPLE 13

Each (1 g) of monoDTPA-EG Ga-DP and bisDTPA-EG Ga-DP as obtained in Example 9 was dissolved in $CHCl_3$-MeOH (1:1) (200 ml), and a theoretical amount of $GdCl_3$ dissolved in water (2 ml) was added thereto to form a complex. The reaction mixture was treated as in Example 11 to give each of the following compounds in a yield of 100%: Gd-monoDTPA-EG Ga-DP and Gd-bisDTPA-EG Ga-DP.

EXAMPLE 14

Each (1 g) of monoDTPA-EG Ga-DP and bisDTPA-EG Ga-DP as obtained in Example 9 was dissolved in $CHCl_3$-MeOH (1:1) (200 ml), and a theoretical amount of $GaCl_3$ dissolved in pyridine (2 ml) was added thereto to form a complex. The reaction mixture was treated as in Example 11 to give each of the following compounds in a yield of 100%: Ga-monoDTPA-EG Ga-DP and Ga-bisDTPA-EG Ga-DP.

EXAMPLE 15

To a solution of hematoporphyrin (1 g) in THF (30 ml), DCHA (2 ml) dissolved in ether (10 ml) was added, whereby the reaction proceeded. Ether was added to the reaction mixture. The precipitated crystals were collected by filtration and washed with ether to give hematoporphyrin DCHA salt (1.4 g). Yield, 90.0%.

EXAMPLE 16

In the same manner as in Example 15, diacetylhematoporphyrin was treated to give diacetylhematoporphyrin DCHA salt (1.4 g). Yield, 94.6%.

EXAMPLE 17

To hematoporphyrin DCHA salt (1 g) as obtained in Example 15, $CHCl_3$ (50 ml) and glycine ethyl ester hydrochloride (0.6 g) were added, and DCC (0.5 g) was dropwise added thereto while stirring, whereby the reaction proceeded in 2 hours. The reaction mixture was allowed to stand overnight and concentrated under reduced pressure. To the residue, ethyl acetate was added, followed by filtration. The filtrate was concentrated under reduced pressure to give HP-Gly-ethyl ester, which was then dissolved in ethanol (50 ml), and N/2 KOH ethanol was added thereto until the hydrolysis was achieved. To the reaction mixture, water was added, followed by filtration. To the filtrate, 10% citric acid was added to make aidic (pH 4), and the precipitated crystals were collected by filtration, washed with water and dried to give HP-Gly (0.8 g). Yield, 71.4%.

EXAMPLE 18

To hematoporphyrin DCHA salt (1 g) as obtained in Example 15, $CHCl_3$ (50 ml) was added, and glutamic acid diethyl ester hydrochloride (0.8 g) was added thereto. The resultant mixture was treated as in Example 17 to give HP-Glu (1.0 g). Yield, 78.1%.

EXAMPLE 19

To a solution of diacetylhematoporphyrin DCHA salt (1 g) as obtained in Example 16 in $CHCl_3$ (50 ml), glycine ethyl ester hydrochloride (0.6 g) was added. The resultant mixture was treated as in Example 17 to give HDA-Gly (0.9 g). Yield, 81.1%.

EXAMPLE 20

To a solution of diacetylhematoporphyrin DCHA salt (1 g) as obtained in Example 16 in $CHCl_3$ (50 ml), glutamic acid diethyl ester hydrochloride (0.8 g) was added. The resultant mixture was treated as in Example 17 to give HDA-Glu (1.1 g). Yield, 87.3%.

EXAMPLE 21

Each (1 g) of HP-Gly-ethyl ester, HP-Glu-diethyl ester, HDA-Gly-ethyl ester and HDA-Glu-diethyl ester was dissolved in acetic acid (50 ml), sodium acetate (200 mg) and $InCl_3$ (200 mg) were added thereto, and the resultant mixture was heated at 100° C. while stirring. To the reaction mixture, physiological saline solution (100 ml) was added, and the precipitated crystals were collected by filtration, washed with water and hydrolyzed with N/2 KOH ethanol. The hydrolyzed mixture was made acidic (pH 4) with 10% citric acid. The precipitated crystals were collected by filtration, washed with water and dried to give In-HP-Gly (0.5 g; yield, 41.0%), In-HP-Glu (0.4 g; yield, 33.3%), In-HDA-Gly (0.4%; yield, 33.1%) or In-HDA-Glu (0.4 g; yield, 33.9%).

EXAMPLE 22

Preparation of a radioactive diagnostic agent comprising $^{111}$In-monoDTPA-EG Ga-DP:

monoDTPA-EG Ga-DP (1.96 mg; 1.68 μmol) was dissolved in sterilized 0.1M citrate buffer (pH 5.7) (2 ml) containing no pyrogen substance, and the resultant solution was passed through a filter (pore size, 0.2 μm) and filled in a vial replaced by nitrogen gas. To the vial, physiological logical saline solution (0.1 ml) containing $^{111}$InCl$_3$ (1.3 mCi) was added, whereby a radioactive diagnostic agent comprising $^{111}$In-monoDTPA-EG Ga-DP was obtained.

The radioactive diagnostic agent as obtained above was developed onto a silica gel thin layer plate using methanol-acetic acid (5:1) as a developing solvent and scanned by the use of a radiochromato-scanner. The radio-activity was detected as a peak at Rf=0.31, and no other radioactive peak was found. In the same manner as above, $^{111}$InCl$_3$ as used for preparation of the radioactive diagnostic agent was subjected to chromatography and gave a radioactive peak at the original point. From the above results, it is understood that the labelling rate of $^{111}$In-monoDTPA-EG Ga-DP in the radioactive diagnostic agent is almost 100%.

EXAMPLE 23

Preparation of a radioactive diagnostic agent comprising $^{111}$In-HP-Gly:

A solution of HP-Gly (1.03 mg; 1.68 μmol) in acetic acid (1 ml) was added to $^{111}$InCl$_3$ (3.3 mCi), followed by stirring by the aid of a ultrasonic vibrator for 5 minutes. The resultant solution was heated in an oil bath (80° C.) for 1 hour and allowed to stand at room temperature. The resultant solution was admixed with water (2 ml) and extracted twice with ethyl acetate (2 ml). The ethyl acetate extracts were combined together, washed with water (2 ml) and dried in vacuo. To the residue, 0.1N NaOH (0.05 ml; 5 μmol) was added, and then 2/15N phosphate buffer (pH 7.4) (2 ml) was added thereto, followed by stirring. The resulting solution was passed through a filter (pore size, 0.2 μm) and filled in a vial replaced by nitrogen gas to give a radioactive diagnostic agent containing $^{111}$In-HP-Gly. Yield, 79.4%.

In the same manner as in Example 22, the radioactive diagnostic agent as obtained above was subjected to test for examination of the radiochemical purity. The radioactivity was detected as a peak at Rf=0.66, and no other radioactive peak was found. From this fact, the radioactive diagnostic agent may be considered to be almost 100% in radiochemical purity.

EXAMPLE 24

Scintigraphy of a radioactive diagnostic agent comprising $^{111}$In-monoDTPA-EG Ga-DP in cancer-bearing hamster:

To a hamster transplanted with pancreatic cancer (Ueda et al: Peptides, 5, 423 (1984)), the radioactive diagnostic agent comprising $^{111}$In-monoDTPA-EG Ga-DP (300 μCi) as obtained in Example 22 was administered intravenously. Scintigraphy was obtained 72 and 96 hours after the administration by the use of a gamma-camera equipped with a medium energy high resolution type collimator. As the result, the locus of cancer could be clearly imaged at both stages, from which it may be understood that the radioactive diagnostic agent is very useful.

EXAMPLE 25

Distribution of a radioactive diagnostic agent comprising $^{111}$In-monoDTPA-EG Ga-DP in cancer-bearing hamster:

To the hamsters as used in Example 24, the radioactive diagnostic agent comprising $^{111}$In-monoDTPA-EG Ga-DP (300 μCi) as obtained in Example 22 or a conventional radioactive diagnostic agent comprising gallium ($^{67}$Ga) citrate (1 mCi) was administered intravenously. With lapse of time, the animals were sacrificed, and the organs were extracted and subjected to measurement of radioactivity and weight, from which the radioactivity level ratio between the cancer and each organ was determined. The results are shown in Tables 2 and 3.

TABLE 2

Distribution of the radioactive diagnostic agent comprising $^{111}$In—monoDTPA—EG Ga—DP in pancreatic cancer bearing hamster (ratio of radioactivity level in cancer to that in organ 96 hours after administration)

| Cancer/Organ | $^{111}$In—monoDTPA—EG Ga—DP |
|---|---|
| Cancer/Liver | 0.53 |
| Cancer/Spleen | 0.43 |
| Cancer/Lung | 1.33 |
| Cancer/Heart | 3.41 |
| Cancer/Kidney | 0.91 |
| Cancer/Blood | 61.89 |

TABLE 3

Distribution of the radioactive
diagnostic agent comprising gallium
($^{67}$Ga) citrate in pancreatic cancer
bearing hamster (ratio of radioactive
level in cancer to that in organ
72 hours after administration)

| Cancer/Organ | Gallium ($^{67}$Ga) citrate |
| --- | --- |
| Cancer/Liver | 0.21 |
| Cancer/Spleen | 0.41 |
| Cancer/Lung | 1.36 |
| Cancer/Heart | 3.02 |
| Cancer/Kidney | 0.91 |
| Cancer/Blood | 7.72 |

From the results as shown in Tables 2 and 3, it is understood that the radioactive diagnostic agent of the invention gives remarkable accumulation in cancer than the conventional radioactive diagnostic agent comprising gallium ($^{67}$Ga) citrate.

EXAMPLE 26

Distribution of a radioactive diagnostic agent comprising $^{111}$In-HP-Gly in cancer-bearing hamster:

To the hamsters as used in Example 24, the radioative diagnostic agent comprising $^{111}$In-HG-Gly (300 μCi) as obtained in Example 23 was adminstered intravenously. With lapse of time, the animals were sacrificed, and the ogans were extracted and subjected to measurement of radioactivity and weight, from which the radioactivity level ratio between the cancer and each organ was determined. The results are shown in Table 4.

TABLE 4

Distribution of the radioactive
diagnostic agent comprising
$^{111}$In—HP—Gly in pancreatic cancer
bearing hamster (ratio of radioactivity
level in cancer to that in organ
organ 72 hours after administration)

| Cancer/Organ | $^{111}$In—HP—Gly |
| --- | --- |
| Cancer/Liver | 0.06 |
| Cancer/Spleen | 0.15 |
| Cancer/Lung | 0.76 |
| Cancer/Heart | 0.93 |
| Cancer/Kidney | 0.17 |
| Cancer/Blood | 33.70 |

From the results as shown in Table 4, it is understood that the radioactive diagnostic agent of the invention gives remarkable accummulation in cancer.

EXAMPLE 27

Preparation of a radioactive diagnostic agent comprising $^{99m}$Tc-monoDTPA-EG Ga-DP:

monoDTPA-EG Ga-DP (1.74 mg; 1.5 μmol) was dissolved in sterilized distilled water (1.5 ml), and sodium hydrosulfite (0.26 mg; 1.5 mmol) was added thereto. The resultant solution was made acidic (pH 5.7) with 0.1N hydrochloric acid, passed through a filter (pore size, 0.2 μm) and filled in a vial replaced by nitrogen gas. To the vial, a physiological saline solution (0.5 ml) containing technetium ($^{99m}$Tc) pertechnetate (5.0 mCi) was added, whereby a radioactive diagnostic agent comprising $^{99m}$Tc-monoDTPA-EG Ga-DP was obtained.

In the same manner as in Example 22, the radioactive diagnostic agent as obtained above was subjected to test for examination of the labelling rate. The radioactivity was detected as a peak at Rf=0.31, and no other radioactive peak was found. Likewise, technetium pertechnetate as used for preparation of the radioactive diagnostic agent was subjected to chromatography and gave a radioactive peak at Rf=0.87. From the above results, it is understood that the labelling rate of $^{99m}$Tc-monoDTPA-EG Ga-DP in the radioactive diagnostic agent is almost 100%.

EXAMPLE 28

Preparation of a radioactive diagnostic agent comprising $^{67}$Ga-DTPA-EG DP-Me:

DTPA-EG DP-Me (1.86 mg; 1.68 μmol) was dissolved in sterilized 0.1M citrate buffer (pH 5.7) (2 ml) containing no pyrogen substance, and the resultant solution was passed through a filter (pore size, 0.2 μm) and filled in a vial replaced by nitrogen gas. To the vial, a physiological saline solution (0.1 ml) contining $^{67}$GaCl$_3$ (1.3 mCi) was added, whereby a radioactive diagnostic agent comprising $^{67}$Ga-DTPA-EG DP-Me was obtained.

In the same manner as in Example 22, the radioactive diagnostic agent as obtained above was subjected to test for examination of the labelling rate. The radioactivity was detected as peaks at Rf=0.31 and at Rf=0.06, which are attributed respectively to monoDTPA-EG DP-Me and bisDTPA-EG DP-Me. Likewise, $^{67}$GaCl$_3$ as used for preparation of the radioactive diagnostic agent was subjected to chromatography and gave a radioactive peak at the original point. From the above results, it is understood that the labelling rate of $^{67}$Ga-DTPA-EG DP-Me in the radioactive diagnostic agent is almost 100%.

EXAMPLE 29

Preparation of a radioactive diagnostic agent comprising $^{111}$In-bisDTPA-EG DP:

In the same manner as in Example 22 but using bisDTPA-EG DP (2.41 mg; 1.68 μmol) in place of monoDTPA-EG Ga-DP, there was prepared a radioacive diagnostic agent comprising $^{111}$In-bisDTPA-EG DP.

In the same manner as in Example 22, the radioactive diagnostic agent as obtained above was subjected to test for examination of the labelling rate. The radioactivity was detected as a peak at Rf=0.06, and no other radioactive peak was found. From this fact, it is understood that the labelling rate of $^{111}$In-bisDTPA-EG DP in the radioactive diagnostic agent is almost 100%.

EXAMPLE 30

Preparation of a radioactive diagnostic agent comprising $^{67}$Ga-HP-Glu:

A solution of HP-glu (1.46 mg; 1.68 μmol) in acetic acid (1 ml) was added to $^{67}$GaCl$_3$ (6.62 mCi), and the resultant mixture was treated as in Example 23 to give a radioactive diagnostic agent comprising $^{67}$Ga-HP-Glu. Yield, 46.5%.

In the same manner as in Example 22, the radioactive diagnostic agent as obtained above was subjected to test for examination of the radiochemical purity. The radioactivity was detected as a peak at Rf=0.83, and no other radioactive peak was found. From this fact, the radioactive diagnostic agent may be considered to be almost 100% in radiochemical purity.

EXAMPLE 31

Bis(pheophorbide) ethylene glycol diester (1 g) was dissolved in 30% hydrobromic acid-acetic acid (25 g), and the resultant mixture was stirred for 15 hours. The reaction mixture was concentrated under reduced pressure to give bis[2-desethenyl-2-(1-bromoethyl)pheophorbide] ethylene glycol diester as crystals. The crystals were dissolved in acetone (50 ml), a solution of NaI (10 g) in acetone (50 ml) was added, and the resultant mixture was stirred while warming for 30 minutes. The reaction mixture was admixed with water (100 ml) and extracted with $CHCl_3$ to give $I_2$ PPB dimer (1.0 g). Yield, 82.0%.

EXAMPLE 32

In the same manner as in Example 9 but using 2,4-bis[1-(3-hydroxypropyl)oxyethyl] Ga-deuteroporphyrin in place of 2,4-bis[1-(2-hydroxyethyl)oxyethyl] Ga-deuteroporphyrin, there was prepared monoDTPA-PG Ga-DP (0.3 g). Yield, 19.8%.

EXAMPLE 33

Preparation of a radioactive diagnostic agent comprising $^{111}$In-mono DTPA-PG Ga-DP.

In the same manner as in Example 22 but using monoDTPA-PG Ga-DP, there was prepared a radioactive diagnostic agent comprising $^{111}$In-mono DTPA-PG Ga-DP.

EXAMPLE 34

Distribution of radioactive diagnostic agents comprising $^{111}$In-monoDTPA-EG Ga-DP, comprising $^{111}$In-monoDTPA-PG Ga-DP and comprising $^{67}$Ga citrate in cancer-bearing and infammation-induced hamsters:

To the hamsters as used in Example 24, turpentine oil (a mixture of alpha-pinene, beta-pinene and 1-limonene (8:1:1 by weight; manufactured by Toyo Hakka) was applied to induce inflammation. The radioactive diagnostic agent comprising $^{111}$In-monoDTPA-EG Ga-DP (760 μCi), $^{111}$In-monoDTPA-PG Ga-DP (760 μCi) or $^{67}$Ga citrate (570 μCi) was administered intravenously to the hamsters, and imaging was made by the use of a gamma-camera at 72 hour post-injection. Then, the animals were sacrificed, and the radioactivity in each tissue was measured. The radioactivity level ratio between the tumor or inflammation and each tissue was determined. The results are shown in Table 5.

TABLE 5

| | Tumor or inflammation to tissue concentration ratio of tumor-imaging agents at 72 hour post-injection | | | | | |
|---|---|---|---|---|---|---|
| | In—111-monoDTPA—EG Ga—DP | | In—111-monoDTPA—PG GA—DP | | Ga—67 citrate | |
| Organ | Tumor | Inflammation | Tumor | Inflammation | Tumor | Inflammation |
| Liver | 0.21 ± 0.06 | 0.21 ± 0.16 | 0.11 ± 0.11 | 0.07 ± 0.04 | 0.18 | 0.33 |
| Spleen | 0.16 ± 0.03 | 0.06 ± 0.01 | 0.13 ± 0.03 | 0.07 ± 0.04 | 0.39 | 0.68 |
| Lung | 0.52 ± 0.33 | 0.21 ± 0.14 | 1.06 ± 0.07 | 0.59 ± 0.27 | 1.26 | 2.23 |
| Heart | 1.14 ± 0.28 | 0.49 ± 0.26 | 1.15 ± 0.33 | 0.52 ± 0.37 | 1.73 | 3.10 |
| Kidney | 0.79 ± 0.08 | 0.33 ± 0.13 | 0.56 ± 0.02 | 0.31 ± 0.16 | 0.20 | 0.36 |
| Blood | 55.75 ± 10.61 | 22.96 ± 9.56 | 44.20 ± 6.05 | 24.49 ± 11.26 | 9.89 | 17.55 |
| Muscle | 22.16 ± 6.53 | 8.71 ± 2.98 | 29.00 ± 7.90 | 15.18 ± 4.37 | 14.20 | 25.15 |

Note:
Presented data were mean and s.d. for 3 animals, or mean for 2 animals.

From the above results, it is understood that $^{111}$In-monoDTPA-EG Ga-DP and $^{111}$In-monoDTPA-PG Ga-DP are nearly equal in affinities to tumor and inflammation. In imaging of inflammation, they are inferior to $^{67}$Ga citrate. In imaging of tumor, they are superior to $^{67}$Ga citrate.

EXAMPLE 35

Distribution of radioactive diagnostic agents comprising $^{111}$In-monoDTPA-EG Ga-DP, comprising $^{111}$In-monoDTPA-PG Ga-DP, comprising $^{111}$In-monoDTPA-EG Zn-DP and comprising $^{67}$Ga citrate in infammation-induced rats:

SD rats of about 200 grams in bodyweight received croton oil (0.1 ml) at the right hind leg subcutaneously to induce inflammation. After 4 days, a radioactive diagnostic agent comprising $^{111}$In-monoDTPA-EG Ga-DP, $^{111}$In-monoDTPA-PG Ga-DP, $^{111}$In-monoDTPA-EG Zn-DP or $^{67}$Ga citrate (0.5 to 1.0 mCi) was intravenously administered to the rats at the tail vein. Imaging was made by the use of a gamma camera 72 hours after the administration. Then, the animals were sacrificed, and the radioactivity in each tissue was measured. The radioactivity level ratio between the inflamation and each tissue was determined. The results are shown in Table 6.

TABLE 6

| | Inflammation to tissue concentration ratio of tumor-imaging agents at 72 hour post-injection | | | |
|---|---|---|---|---|
| Inflammation/Tissue | $^{111}$In—monoDTPA—EG Ga—DP | $^{111}$In—monoDTPA—PG Ga—DP | $^{111}$In—monoDTPA—EG Zn—DP | $^{67}$Ga citrate |
| Liver | 0.14 ± 0.04 | 0.08 ± 0.02 | 0.33 | 0.69 ± 0.17 |
| Spleen | 0.18 ± 0.03 | 0.13 ± 0.03 | 0.28 | 0.64 ± 0.11 |
| Lung | 1.43 ± 0.32 | 1.55 ± 0.40 | 1.70 | 5.41 ± 0.71 |
| Heart | 2.40 ± 0.63 | 1.93 ± 0.60 | 2.08 | 7.49 ± 3.37 |
| Kidney | 1.42 ± 0.35 | 0.79 ± 0.15 | 1.33 | 5.04 ± 6.35 |
| Blood | 185.25 ± 82.70 | 108.00 ± 38.52 | 104.05 | 21.61 ± 6.47 |
| Muscle | 19.23 ± 10.45 | 25.14 ± 7.67 | 8.38 | 12.81 ± 4.61 |

Note:
Presented data were mean and s.d. for 3 animals.

From the above results, it is understood that $^{111}$In-monoDTPA-EG Ga-DP, $^{111}$In-monoDTPA-PG Ga-DP and $^{111}$In-monoDTPA-EG Zn-DP show much lesser accumulation in inflammation than $^{67}$Ga citrate. Accordingly, they are more suitable for detection of cancers than $^{67}$Ga citrate.

What is claimed is:

1. A porphyrin compound of formula:

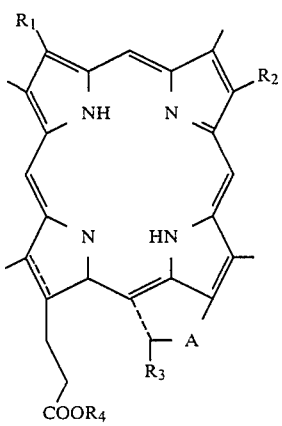

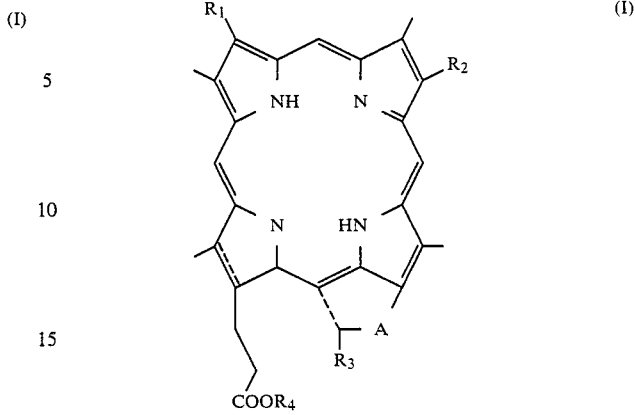

wherein
R₁ and R₂ are each —CH=CH₂, —CH₂CH₃, —CH-(O-lower alkanoyl)CH₃; —CH(OR)CH₃ or —CH-(O-lower alkylene-OR)CH₃;

R₃ is —H, —COOH, —COO-lower alkyl, —COO-lower alkylene-OR or —COO-lower alkylene-OOC—Z;

R₄ is —H, -lower alkyl or -lower alkylene-OR;

R is —H, —lower alkyl or a residue of a polyfunctional compound, said polyfunctional compound containing as one functional group carboxyl and at least one additional functional group which is selected from the group consisting of amino; hydroxy; mercapto and carboxyl;

Z is a residue of the compound of the formula (I) excluding R₃ therefrom;

A is —CH₂— or —CO—; and the dotted line from the gamma-position indicates no bonding or a single direct bond; and the dotted line between the 7- and 8-positions indicates the presence of a single bond or a double bond;

and its complexes with a metal(s) in the porphine skeleton and/or at the residue of the polyfunctional compound, at least one or R₁, R₂, R₃ and R₄ being a group containing R which represents the residue of the polyfunctional compound and R₁ being capable of representing 1-iodoethyl in addition to said meanings when R₃ is —COO-lower alkylene-OOC—Z.

2. The porphyrin compound according to claim 1, wherein a is —CH₂—, the dotted line from the gamma-position indicates no bodnding and the dotted line between the 7- and 8-positions indicates the presence of a double bond.

3. The porphyrin compound according to claim 1, wherein A is —CO—, the dotted line from the gamma-position indicates a single direct bond and th dotted line between the 7- and 8-positions indicates the presence of a single bond.

4. A porphyrin compound of the formula:

wherein
R₁ and R₂ are each —CH=CH₂, —CH₂CH₃, —CH-(O-lower alkanoyl)CH₃, —CH(OR)CH₃ or —CH-(O-lower alkylene-OR)CH₃;

R₃ is —H, —COOH, —COO-lower alkyl, —COO-lower alkylene-OR or —COO-lower alkylene-OOC—Z;

R₄ is —H, —lower alkyl or -lower alkylene —OR;

R is —H, -lower alkyl or a residue of a polyfunctional compound, said polyfunctional compound containing as one functional group carboxyl and at least one additional functional group which is a chelate-forming group;

Z is a residue of the compound of the formula (I) excluding R₃ therefrom;

A is —CH₂— or —CO—; and the dotted line from the gamma-position indicates no bonding or a single direct bond; and the dotted line between the 7- and 8-positions indicates the presence of a single bond or a double bond;

and its complexes with a metal(s) in the porphine skeleton and/or at the residue of the polyfunctional compound, at least one of R₁, R₂, R₃ and R₄ being a group containing R which represents the residue of the polyfunctional compound and R₁ being capable of representing 1-iodoethyl in addition to said meanings when R₃ is —COO-lower alkylene-OOC—Z.

5. The porphyrin compound according to claim 4, wherein said polyfunctional compound is selected from the group consisting of ethylenediaminetetracetic acid. diethylenetriaminepentaacetic acid, 1,2-bis(o-aminophenoxy) ethane-N,N,N',N'-tetracetic acid, 1,3diamoninopropan-2-ol-N,N,N',N'-tetraacetic acid, trans-1,2-cyclohexanediamine-N,N,N',N'-tetraacetic acid, N-hydroxyethylethylenediamine-N,N',N'- triacetic acid, ethylenediamine-N,N'-diacetic acid, iminodiacetic acid and ethylenediaminedi(o-hydroxyphenylacetic acid).

6. The porphyrin compound according to claim 5, wherein said polyfunctional compound is diethylenetriaminepentaacetic acid.

7. The porphyrin compound according to claim 5, wherein said polyfunctional compound is trans1,2-cyclohexanediamine-N,N,N',N'-tetraacetic acid.

8. The porphyrin compound according to claim 1, wherein said polyfunctional compound is an amino acid.

9. The porphyrin compound according to claim 8, wherein said amino acid is selected from the group consisting of glycine, cysteine, glutamic acid, alanine, cystine, asparagine, valine, methionine, glutamine, leucine, phenylalanine, isoleucine, serine, tryptophane, threonine and aspartic acid.

10. The porphyrin compound according to claim 9, wherein the amino acid is glycine.

11. The porphyrin compound according to claim 9, wherein the amino acid is glutamic acid.

12. The complex of the porphyrin compound according to claim 1, wherein the metal is present in the porphine skeleton.

13. The complex of the porphyrin compound according to claim 1, wherein the metal is present at the residue of the polyfunctional carboxyl compound.

14. The complex of the porphyrin compound according to claim 1, wherein the metals are present in the porphine skeleton and at the residue of the polyfunctional carboxyl compound.

15. The complex of the porphyrin compound according to claim 1, wherein the metals are chosen from Si, Mn, Fe, Co, Ni, Zn, Ga, In, Sn, Sm, Eu, Gd, Tc and Tl.

16. The complex of the porphyrin compound according to claim 1, wherein at least one metal is radioactive.

17. A radioactive diagnostic composition comprising carrier and the complex of the porphyrine compound according to claim 1, wherein at least one metal is radioactive.

* * * * *

UNITED STATES PATENT AND TRADEMARK OFFICE
CERTIFICATE OF CORRECTION

PATENT NO. : 4,849,207

DATED : July 18, 1989

INVENTOR(S) : Isao Sakata et al

It is certified that error appears in the above-identified patent and that said Letters Patent is hereby corrected as shown below:

Claim 1, (column 19, line 49), "or" should be --of--.

Claim 2 (column 19, line 57), "a" should be --A--.

Claim 2 (column 19, line 59), "bodnding" should be --bonding--.

Claim 5 (column 20, line 53), "tetracetic" should be --tetraacetic--.

Claim 7 (column 20, line 64), "trans1,2" should be --trans-1,2--.

Signed and Sealed this

Twenty-second Day of May, 1990

*Attest:*

HARRY F. MANBECK, JR.

*Attesting Officer*     *Commissioner of Patents and Trademarks*